United States Patent [19]

Guselnikov et al.

[11] 4,328,350
[45] May 4, 1982

[54] 1,1,2,2-TETRAMETHYL-1,2-DISILACYCLOBUTANE AND METHOD FOR PREPARING SAME

[76] Inventors: Leonid E. Guselnikov, Yasenevo, 4 mikroraion, 6"V", kv. 394; Jury P. Polyakov, Dmitrovskoe shosse, 96, korpus 1, kv. 55, both of Moscow; Elvira A. Volnina, ulitsa Oktyabrskaya, 1, Scherbinka Moskovskoi oblasti; Nikolai S. Nametkin, Leninsky prospekt, 13, kv. 11, Moscow, all of U.S.S.R.

[21] Appl. No.: 195,608

[22] PCT Filed: Jun. 15, 1979

[86] PCT No.: PCT/SU79/00037

§ 371 Date: Apr. 30, 1980

§ 102(e) Date: Apr. 30, 1980

[87] PCT Pub. No.: WO80/00445

PCT Pub. Date: Mar. 20, 1980

[30] Foreign Application Priority Data

Aug. 30, 1978 [SU] U.S.S.R. .................. 2650451

[51] Int. Cl.$^3$ .............................................. C07F 7/08
[52] U.S. Cl. .................................................. 556/406
[58] Field of Search ........................................ 556/406

[56] References Cited

U.S. PATENT DOCUMENTS

| | | | |
|---|---|---|---|
| 2,850,514 | 9/1958 | Knoth | 556/406 X |
| 3,178,392 | 4/1965 | Kriner | 556/406 X |
| 3,293,194 | 12/1966 | Lovie et al. | 556/406 X |
| 3,445,495 | 5/1969 | Nelson | 556/406 X |
| 3,527,781 | 9/1970 | Levin | 556/406 |

OTHER PUBLICATIONS

Harris et al., "J.A.C.S.", 101, 1979, p. 83.
Seyferth et al., "J.A.C.S.", 100, 1978, p. 7734.
Seyferth et al., "J. Organometal. Chem.", 125, 1977, p. 11.
Ishikawa et al., "J.A.C.S.", 101, 1979, p. 1348.

*Primary Examiner*—Paul F. Shaver
*Attorney, Agent, or Firm*—Fleit & Jacobson

[57] ABSTRACT

A novel chemical compound, viz. 1,1,2,2-tetramethyl-1,2-disilacyclobutane has the formula:

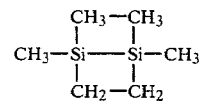

A method for preparing 1,1,2,2-tetramethyl-1,2-disilacyclobutane comprises reacting vapors of 1,2-bis(dimethylchlorosilyl)ethane with vapors of metallic sodium and/or potassium at a temperature within the range of from 250° to 380° C. under a pressure of vapors of 1,2-bis(dimethylchlorosilyl)ethane of from 0.1 to 10 mm Hg, followed by condensation of vapors of the resultant desired product.

4 Claims, No Drawings

1,1,2,2-TETRAMETHYL-1,2-DISILACYCLOBUTANE AND METHOD FOR PREPARING SAME

FIELD OF THE INVENTION

The present invention relates to organo-silicon monomers and, more specifically, to a novel chemical compound—1,1,2,2-tetramethyl-1,2-disilacyclobutane.

STATE OF ART

This compound and its derivatives containing no substituents at the endocyclic carbon atoms have not been hitherto known in the art.

DISCLOSURE OF THE INVENTION

In accordance with the present invention, the novel compound 1,1,2,2-tetramethyl-1,2-disilacyclobutane has the formula:

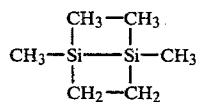

1,1,2,2-Tetramethyl-1,2-disilacyclobutane is a transparent liquid with a geranium scent, boiling at 45°–46° C./29 mm Hg. The monomer polymerizes even at room temperature. However, away from oxygen and moisture, it can be stored for a long time at a temperature below −70° C. The monomer structure has been justified by mass-spectrum, NMR-spectrum: $^1$H and $^{13}$C, as well as by chemical properties. Thus, the peak of a molecular ion in the mass-spectrum corresponds to m/e 144 (47%). In addition thereto, there are observed peaks of fragment ions caused by loss of a methyl group m/e 129 (61%), ethylene m/e 116 (100%) and a successive loss of these two groups m/e 101 (72%) from the molecular ion.

NMR spectra of 1,1,2,2-tetramethyl-1,2-disilacyclobutane present signals: $\delta^1H_{(Si-CH3)}=0.22$ p.p.m. (12H,s), $\delta^1H_{(CH2)}=0.63$ p.p.m. (4H,s); $\delta^{13}C_{(Si-CH3)}=2.95$ p.p.m. (4C), $\delta^{13}C_{(CH2)}=8.70$ p.p.m. (2C).

The ratio between intensities of signals of protons and carbon nuclei of methyl and methylene groups corresponds to the above-given structure of the monomer.

Described hereinbelow are certain chemical transformations which confirm the structure of 1,1,2,2-tetramethyl-1,2-disilacyclobutane:

1. POLYMERIZATION

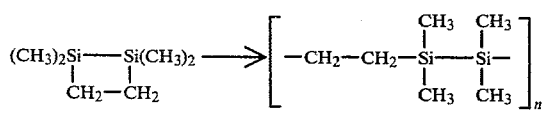

An ampule containing 1.84 g of 1,1,2,2-tetramethyl-1,2-disilacyclobutane is heated to the temperature of 20° C. and its contents are poured into a 10-fold volume of benzene. A white precipitate of the polymer is formed which is filtered-off after 24 hours, washed with pure benzene and dried under vacuum. The weight of the resulting polymer is 1.48 g (80.5% of the theoretical yield), intrinsic viscosity (benzene solution of the polymer) [ζ]=0.22 dl/g (at the temperature of 60° C.).

Elemental Composition of the polymer:

|  | C | H | Si |
|---|---|---|---|
| found, %: | 50.01 | 11.12 | 38.76 |
| calculated, %: | 50.00 | 11.11 | 38.89 |
| for the fragment: | | | |

$$\left[-CH_2-CH_2-\underset{\underset{CH_3}{|}}{\overset{\overset{CH_3}{|}}{Si}}-\underset{\underset{CH_3}{|}}{\overset{\overset{CH_3}{|}}{Si}}-\right]$$

In the IR-spectrum of the polymer there are bands of 828 cm$^{-1}$ and 1,237 cm$^{-1}$ corresponding to valence vibrations of the group=Si(CH$_3$)$_2$; bands of 2,944 and 2,877 cm$^{-1}$ corresponding to valence vibrations of C—H in methyl and methylene groups and bands of 1,050 and 1,126 cm$^{-1}$ characteristic for the grouping-≡Si—CH$_2$—CH$_2$—Si≡.

In the combination scattering spectrum there is observed the band of 385 cm$^{-1}$ corresponding to valence vibrations of the bond≡Si—Si≡.

NMR-spectra of a benzene solution of the polymer have signals: $\delta^1H_{(Si-CH3)}=0.275$ p.p.m. (12H,s), $\delta^1H_{CH2}=0.875$ p.p.m. (4H,s); $\delta^{13}C_{(Si-CH3)}=0.4$ p.p.m. (4C), $\delta^{13}C_{(CH2)}=13.84$ p.p.m. (2C).

The ratio between signal intensities of carbon nuclei protons of methyl and methylene groups corresponds to the above-given structure of the monomer unit.

2. Chlorination

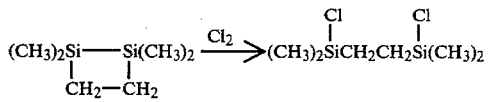

1.43 g of 1,1,2,2-tetramethyl-1,2-disilacyclobutane is charged into a flask and gaseous chlorine diluted with argon is bubbled therethrough for one hour at the temperature of −20° C. On expiration of this time, the resulting reaction mixture is gradually heated, without stopping bubbling, to the temperature of 60° C. for two hours. There are obtained 2.08 g (99.0% of the theoretical yield) of 1,2-bis(dimethylchlorosilyl)ethane. B.p. 198° C., M.p. 36.5° C. which corresponds to the data known from the literature.

3. OXIDATION

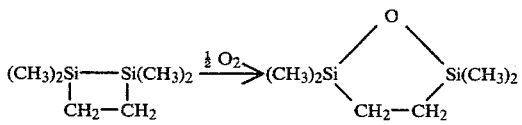

Air is bubbled for 10 hours through 1.49 g of 1,1,2,2-tetramethyl-1,2-disilacyclobutane at the temperature of −10° C. Then the reaction mixture is distilled in vacuum. There are obtained 0.42 g (28.2% of the theoretical yield) of 1,1,3,3-tetramethyl-2-oxa-1,3-disilacyclopentane.

The mass-spectrum: m/e: 160 (M)$^+$, 145 (M-15)$^+$, 132 (M-28)$^+$, n$_D^{20}$=1.4147; d$_4^{20}$=0.862 which corresponds to the data known from the literature.

4. PYROLYSIS

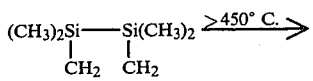

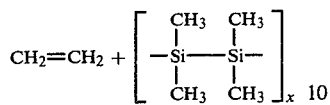

wherein x is an integer of at most 10.

1.86 g of 1,1,2,2-tetramethyl-1,2-disilacyclobutane are passed as vapours under a pressure of from 5.0 to 5.5 mm Hg in a current of dry helium (10 ml/min) through a quartz tube heated to a temperature of 550° to 560° C. The pyrolysis products are collected in a trap cooled with liquid nitrogen. The main gaseous reaction product is ethylene (identified by mass-spectroscopy and chromatography).

1,1,2,2-Tetramethyl-1,2-disilacyclobutane can be used for the preparation of a linear crystalline high-molecular heterochain polymer with a hitherto unknown structure of the monomer unit consisting of alternating dimethylene and methylsubstituted disilene groupings:

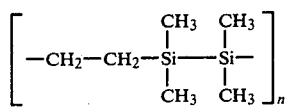

wherein n ranges from 800 to 1,000.

This polymer features a number of valuable properties such as insolubility at a temperature within the range of from −70° to +50° C. in such solvents as alcohols (methanol, ethanol), ketones (acetone, methylethylketone), ethers and esters (diethyl ether, ethylacetate), haloderivatives of hydrocarbons (carbon tetrachloride, chloroform, dichloroethane, trichloroethylene), paraffin (pentane, hexane, heptane, octane), naphthene cyclohexane) and aromatic (benzene, toluene, o-, m- and p-xylenes). The polymer is resistant to the effect of concentrated aqueous solutions of acids (sulphuric acid, nitric acid and hydrochloric acid) and alkalis (caustic soda and caustic potash), effect of light and moisture. Furthermore, the polymer is well machinable by cutting tools, is also well mouldable by hot-compression moulding, and has a good adherence to glass. Articles manufactured from the polymer retain their shape for a long time at a temperature within the range of from −70° to +95° C. The polymer is useful as a gasoline-resistant material in fuel systems of automobiles, for the manufacture of gasoline-resistant gaskets stable in aggressive media and protective coatings.

The method for preparing 1,1,2,2-tetramethyl-1,2-disilacyclobutane according to the present invention consists in that vapours of 1,2-bis(dimethylchlorosilyl)ethane are reacted with vapours of metallic sodium and/or potassium at a temperature within the range of from 250° to 380° C. and under pressure of vapours of 1,2-bis(dimethylchlorosilyl)ethane of from 0.1 to 10 mm Hg, followed by condensation of vapours of the resulting desired product.

The range of pressures of from 0.1 to 10 mm Hg is defined by a partial pressure of vapours of 1,2-bis(dimethylchlorosilyl)ethane. The use of pressures above 10 mm Hg results in clogging of the reactor with densified products, while pressures below 0.1 mm Hg cause lowered productivity of the plant and a reduced yield of the desired product.

As it has been mentioned hereinabove, the reaction of vapours of 1,2-bis(dimethylchlorosilyl)ethane is effected with vapours of sodium and/or potassium. The highest yield of the desired product is ensured upon the interaction of a mixture of vapours of sodium and potassium.

In the reaction of vapours of 1,2-bis(dimethylchlorosilyl)ethane with vapours of sodium and/or potassium under the selected conditions volatile products are formed which contain up to 90-95% of the monomer 1,1,2,2-tetramethyl-1,2-disilacyclobutane.

To remove the impurities contaminating the desired product, the desired product condensate is subjected to distillation under vacuum of from 1 to 15 mm Hg at a temperature within the range of from 0° to 20° C. The boiling point of pure 1,1,2,2-tetramethyl-1,2-disilacyclobutane is 18°-20° C./15 mm Hg.

To facilitate the process control over the predetermined parameters of interaction of vapours of 1,2-bis(-dimethylchlorosilyl)ethane with vapours of sodium and/or potassium, it is advisable that the process be carried out in a current of an inert gas under its pressure of from 50 to 760 mm Hg. This permits the variation of contact time at constant velocity of supplied gaseous 1,2-bis (dimethylchlororosilyl)ethane.

As the inert gas use may be made of any inert gas, preferably nitrogen, helium.

The process for preparing 1,1,2,2-tetramethyl-1,2-disilacyclobutane can be commercially implemented on a continuous basis. The starting 1,2-bis(dimethylchlorosilyl)ethane is a readily available raw material, since it can be easily produced from acetylene and dimethylchlorosilane—an organosilicon monomer which is a product resulting from a commercial synthesis of methylchlorosilanes.

MOST PREFERRED EMBODIMENT OF THE INVENTION

Into a reactor provided with an external electric heating sodium and potassium are charged in a current of a dry inert gas such as argon or nitrogen. The reactor is connected with a system of traps and a vacuum pump. Into a vessel for the starting material also provided with an electric heating 1,2-bis(dimethylchlorosilyl)ethane is charged.The vessel for the starting material is connected with the reactor by means of a pipe having a stopcock. When a required temperature (250° to 380° C.) is reached, the concentration of vapours of alkali metals necessary for the process is obtained. Vapours of 1,2-bis(dimethylchlorosilyl)ethane are passed from the vessel for the starting material to the reactor. The rate of supply of vapours of 1,2-bis(dimethylchlorosilyl)ethane from the vessel for the starting material is controlled by its heating temperature (15° to 90° C.). The pressure of the starting material vapours is within the range of from 0.1 to 10 mm Hg. A dry inert gas such as helium, nitrogen is supplied into the reactor under a pressure of from 50 to 760 mm Hg simultaneously with vapours of 1,2-bis(dimethylchlorosilyl)ethane.

The volatile products formed in the reactor and containing 1,1,2,2-tetramethyl-1,2-disilacyclobutane (up to 90-95%) are passed into a trap cooled with dry ice or liquid nitrogen with the formation of a condensate. Then the condensed volatile products containing 1,1,2,2-tetramethyl-1,2-disilacyclobutane are subjected, for the purpose of the removal of impurities, to distillation in vacuum of 5 mm Hg at the temperature of 8°–10° C. The resulting fraction is condensed in a trap cooled with dry ice.

EXAMPLE 1

Into a reactor provided with an external electric heating 16 g of a mixture of sodium and potassium (at the atomic ratio between sodium and potassium of 1:1) are charged in a current of dry argon. The reactor is connected with a system of traps and a vacuum pump. Into the vessel for the starting material there are charged 10.7 g of 1,2-bis(dimethylchlorosilyl)ethane. The vessel for the starting material is connected with the reactor by means of a pipe provided with a stopcock. The contents of the reactor and the vessel for the starting material are heated. When the temperature in the reactor is made equal to 250°–260° C. and the temperature of 1,2-bis(dimethylchlorosilyl)ethane equals to 55°–60° C., the vacuum pump is switched on and the stopcock is carefully opened. The starting 1,2-bis(dimethylchlorosilyl)ethane in the form of vapours is fed into the reactor under the pressure of 1.0–1.1 mm Hg. The resulting volatile products are passed into a trap cooled with liquid nitrogen. The resulting condensate is distilled in vacuum (18°–20° C./15 mm Hg). The final product is obtained as a transparent liquid which is placed into an ampule, sealed and kept in a Dewar flask with dry ice. The weight of the thus-prepared 1,1,2,2-tetramethyl-1,2-disilacyclobutane is 3.67 g (51.0% of the theoretical yield).

EXAMPLE 2

1,1,2,2-tetramethyl-1,2-disilacyclobutane is prepared following the procedure described in the foregoing Example 1, except that the process is carried out at a temperature inside the reactor of 280°–290° C.

The weight of the resulting 1,1,2,2-tetramethyl-1,2-disilacyclobutane is 3.39 g (47.1% of the theoretical yield).

EXAMPLE 3

1,1,2,2-Tetramethyl-1,2-disilacyclobutane is prepared following the procedure described in Example 1, except that the process is carried in the reactor at a temperature of 370°–380° C.

The weight of the resulting 1,1,2,2-tetramethyl-1,2-disilacyclobutane is 2.90 g (40.3% of the theoretical yield).

EXAMPLE 4

1,1,2,2-tetramethyl-1,2-disilacyclobutane is prepared following the procedure described in Example 1, except that the process is conducted in a current of dry helium supplied under the pressure of 50 mm Hg.

The weight of the resulting 1,1,2,2-tetramethyl-1,2-disilacyclobutane is 3.53 g (49.0% of the theoretical yield).

EXAMPLE 5

1,1,2,2-Tetramethyl-1,2-disilacyclobutane is prepared following the procedure described in Example 1 hereinbefore, except that the process is carried out in a current of dry argon supplied under the pressure of 760 mm Hg.

The weight of the resulting 1,1,2,2-tetramethyl-1,2-disilacyclobutane is 3.29 g (45.7% of the theoretical yield).

EXAMPLE 6

1,1,2,2-Tetramethyl-1,2-disilacyclobutane is prepared following the procedure described in Example 1, except that into the reactor there are charged 16 g of a mixture of sodium and potassium (in the atomic ratio therebetween of 1:3 respectively) and into the vessel for the starting material there are charged 10.7 g of 1,2-bis(dimethylchlorosilyl)ethane maintained at a temperature of from 15° to 20° C. The pressure of saturated vapours of 1,2-bis(dimethylchlorosilyl)ethane is maintained within the range of from 0.10 to 0.15 mm Hg. The process is carried out at a temperature in the reactor of from 300° to 310° C. in a current of dry nitrogen supplied under the pressure of 200 mm Hg.

The weight of the resulting 1,1,2,2-tetramethyl-1,2-disilacyclobutane is 3.46 g (48.1% of the theoretical yield).

EXAMPLE 7

1,1,2,2-Tetramethyl-1,2-disilacyclobutane is prepared following the procedure described in Example 1, except that into the reactor 16 g of a mixture of sodium and potassium (in the atomic ratio therebetween of 3:1) are charged and into the vessel for the starting material there are charged 10.7 g of 1,2-bis(dimethylchlorosilyl)ethane at a temperature thereof of 80° to 90° C. The pressure of vapours of 1,2-bis(dimethylchlorosilyl)ethane is 9.9–10 mm Hg. The process is carried out in a current of dry helium supplied under the pressure of 400 mm Hg, at a temperature of from 300° to 310° C. in the reactor.

The weight of the resulting 1,1,2,2-tetramethyl-1,2-disilacyclobutane is 3.43 g (47.7% of the theoretical yield).

EXAMPLE 8

1,1,2,2-Tetramethyl-1,2-disilacyclobutane is prepared by the procedure described in Example 1, except that the condensate of the desired product is subjected to distillation in vacuum (8°–10° C./5 mm Hg).

The weight of the resulting 1,1,2,2-tetramethyl-1,2-disilacyclobutane is equal to 3.85 g (48% of the theoretical yield).

EXAMPLE 9

Into the upper section of a tubular type reactor sodium and potassium pre-heated to a temperature of from 100° to 110° C. are supplied through a nozzle (in the atomic ratio of 1:3 respectively). Saturated vapours of 1,2-bis(dimethylchlorosilyl)ethane are fed into the same section of the reactor in a current of dry helium under the pressure of 200 mm Hg. Temperature of 1,2-bis(dimethylchlorosilyl)ethane is maintained at 70°–75° C., pressure - 4.0–4.5 mm Hg. In the medium section of the reactor, wherein temperature is equal to 370°–380° C., potassium and sodium are sublimed and their vapours react with vapours of 1,2-bis(dimethylchlorosilyl)ethane. The nonvolatile reaction products formed in the reactor, the unreacted sodium and potassium are condensed in the lower section of the reactor and flow down into a special vessel, while the volatile reaction products containing mainly 1,1,2,2-tetramethyl-1,2-disilacyclobutane are passed, through an outlet pipe in the lower section of the reactor, to a trap cooled with dry ice. As a result, a condensate is formed. The resulting condensate is distilled in vacuum (18°–20° C./15 mm Hg) and the desired product is thus obtained. The resulting product is sealed in an ampule and kept in a Dewar bottle with dry ice.

The weight of the thus-prepared 1,1,2,2-tetramethyl-1,2-disilacyclobutane is 3.69 g (51.2% of the theoretical yield).

EXAMPLE 10

1,1,2,2-Tetramethyl-1,2-disilacyclobutane is prepared following the procedure described in the foregoing Example 9, except that the condensate of the desired product is subjected to distillation in vacuum (0°–2° C./1 mm Hg).

The weight of the thus-prepared 1,1,2,2-tetramethyl-1,2-disilacyclobutane is 4.47 g (62% of the theoretical yield).

INDUSTRIAL APPLICABILITY

The novel compound according to the present invention, namely 1,1,2,2-tetramethyl-1,2-disilacyclobutane is useful as a monomer for the production of a polymeric material featuring plastic properties, a high gasoline - and oil-resistance.

The method for preparing the monomer according to the present invention can be readily implemented on a commercial scale; it is quite simple and efficient and useful in the industry of the heteroorganic synthesis.

We claim:

1. 1,1,2,2-Tetramethyl-1,2-disilacyclobutane of the formula:

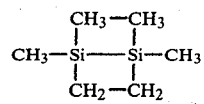

2. A method for preparing 1,1,2,2-tetramethyl-1,2-disilacyclobutane according to claim 1, characterized in that vapours of 1,2-bis(dimethylchlorosilyl)ethane are reacted with vapours of metallic sodium and/or potassium at a temperature within the range of from 250° to 380° C. under a pressure of vapours of 1,2-bis(dimethylchlorosilyl)ethane of from 0.1 to 10 mm Hg, followed by condensation of vapours of the resulting desired product.

3. A method according to claim 2, characterized in that the condensate of vapours of the desired product is subjected to distillation in vacuum of 1–15 mm Hg at a temperature within the range of from 0° to 20° C.

4. A method according to claims 2 or 3, characterized in that the reaction of vapours of 1,2-bis(dimethylchlorosilyl)ethane with vapours of metallic sodium and/or potassium is effected in a current of an inert gas under a pressure of said gas ranging from 50 to 760 mm Hg.

* * * * *